(12) United States Patent
Ramakrishnan et al.

(10) Patent No.: US 12,398,185 B2
(45) Date of Patent: Aug. 26, 2025

(54) PEPTOID BLOCKING O-GlcNAcylated NF-kappaB c-Rel

(71) Applicant: Case Western Reserve University, Cleveland, OH (US)

(72) Inventors: Parameswaran Ramakrishnan, Solon, OH (US); Jonathan K. Pokorski, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 940 days.

(21) Appl. No.: 17/595,960

(22) PCT Filed: May 28, 2020

(86) PCT No.: PCT/US2020/034796
§ 371 (c)(1),
(2) Date: Nov. 30, 2021

(87) PCT Pub. No.: WO2020/243226
PCT Pub. Date: Dec. 3, 2020

(65) Prior Publication Data
US 2022/0259275 A1 Aug. 18, 2022

Related U.S. Application Data (60) Provisional application No. 62/855,180, filed on May 31, 2019.

(51) Int. Cl.
| | |
|---|---|
| C07K 14/47 | (2006.01) |
| A61P 35/02 | (2006.01) |
| A61P 37/00 | (2006.01) |
| A61K 38/00 | (2006.01) |

(52) U.S. Cl.
CPC .......... C07K 14/4703 (2013.01); A61P 35/02 (2018.01); A61P 37/00 (2018.01); A61K 38/00 (2013.01)

(58) Field of Classification Search
CPC ...... C07K 14/4703; A61P 35/02; A61P 37/00; A61P 3/10; A61P 43/00; A61K 38/00; A61K 45/06
See application file for complete search history.

(56) References Cited

U.S. PATENT DOCUMENTS

| 9,696,296 B2 | 7/2017 | Ramakrishnan et al. |
| 2012/0237552 A1* | 9/2012 | Moreno ................. A61P 25/28 514/17.7 |

OTHER PUBLICATIONS

International Search Report issued for corresponding International Application No. PCT/US2020/034796 dated Aug. 12, 2020, 2 pages.
Khan et al., "Ring-Closing Metathesis Approaches for the Solid-Phase Synthesis of Cyclic Peptoids," Organic Letters, 2011, vol. 13, No. 7, 4 pages.
Patch et al., "Versatile Oligo (N-Substituted) Glycines: The Many Roles of Peptoids in Drug Discovery," Pseudo-peptides in Drug Development, 2004, 31 pages.
Ramakrishnan et al., "Targeting c-Rel O-GlcNAcylation to control hyperglycemia-dependent transcription in T lymphocytes," The Journal of Immunology, May 2020, 2 pages.
Hart et al., "Cycling of O-linked β-N-acetylglucosamine on nucleocytoplasmic proteins," Nature, Apr. 2007, vol. 446, 6 pages.
Ramakrishnan et al., "Activation of the Transcriptional Function of the NF-κB Protein c-Rel by O-GlcNAc Glycosylation," Sci Signal, 2013, 30 pages.
Ramakrishnan et al., "Deficiency of Nuclear Factor-kB c-Rel Accelerates the Development of Autoimmune Diabetes in NOD Mice," Diabetes, Aug. 2016, vol. 65, 13 pages.
De Jesus et al., "NF-kappaB c-Rel Dictates the Inflammatory Threshold by Acting as a Transcriptional Repressor," Science, Mar. 2020, 32 pages.

* cited by examiner

*Primary Examiner* — Sudhakar Katakam
(74) *Attorney, Agent, or Firm* — Tarolli, Sundheim, Covell & Tummino LLP (57) ABSTRACT

The present disclosure relates to peptoids for inhibiting O-GlcNAcylated proteins, and in particular, the c-Rel peptide of NF-kappaB. The compounds can be used in the prevention or treatment of diseases of conditions having elevated levels of O-GlcNAcylation, such as autoimmune diseases, conditions that are related to hyperglycemia, or cancers.

9 Claims, 6 Drawing Sheets
(1 of 6 Drawing Sheet(s) Filed in Color)

PEPTOID BLOCKING O-GlcNAcylated NF-kappaB c-Rel

CROSS-REFERENCE TO RELATED APPLICATIONS

This is a National Stage application of PCT international application PCT/US2020/034796, filed May 28, 2020, which claims the benefit of U.S. Provisional Application No. 62/855,180 filed May 31, 2019, both of which are hereby incorporated by reference in its entireties.

RELATED APPLICATIONS

This application claims the benefit of U.S. Provisional Application No. 62/855,180 filed May 31, 2019, which is hereby incorporated by reference in its entirety.

STATEMENT REGARDING FEDERALLY SPONSORED RESEARCH OR DEVELOPMENT

This invention was made in part with grants from National Institutes of Health: R01AI116730, entitled "Transcriptional regulation by O-GlcNAcylation in T lymphocytes"; R21AI144264, entitled "Regulation of B cell function and antibody class switching by c-Rel O-GlcNAcylation" and Institutional CTSC UL1TR000439 from the National Center for Advancing Translational Sciences, entitled "To develop novel therapeutics for type 1 diabetes". The U.S. government may have certain rights in the invention.

TECHNICAL FIELD

The disclosure relates generally to inhibiting the transcription factor nuclear factor kappa B (NF-kappaB) protein. More specifically, this disclosure relates to methods of inhibiting the subunit of NF-kappaB c-Rel in its O-GlcNAcylated state, and even more specifically, at serine reside 350 using the novel peptoid disclosed herein. Such inhibition can be used to treat or prevent disease states in which O-GlcNAcylation has been implicated, including various autoimmune diseases and some cancers.

BACKGROUND

The precise regulation of transcription is essential for productive immune response and prevention of autoimmunity. Type 1 diabetes is an auto immune disorder in which self-reactive T cells destroy insulin producing pancreatic beta cells. Deficiency of insulin leads to hyperglycemia, which is a defining characteristic of autoimmune diabetes. One of the pathological consequences of hyperglycemia is aberrant posttranslational modification of cellular proteins in a process called O-GlcNAcylation. It is a reversible intracellular posttranslational modification that occurs in the cytoplasm and nucleus. It involves attachment of the sugar, N-acetylglucosamine (GlcNAc), to the serine and threonine residues in nuclear and cytoplasmic proteins. Analogous to phosphorylation, modification by O-GlcNAc is a dynamic process, mediated by the enzymes O-GlcNAc transferases (OGT) for the addition and O-GlcNAcase (OGA) for the removal of O-GlcNAc from proteins. O-GlcNAcylation levels play an important role in nearly all cellular processes including cell cycle, transcription, translation, protein stability, protein interactions, cellular stress and immune functions. Lack of O-GlcNAcylation is embryonically lethal. However, compared to phosphorylation, O-GlcNAcylation is a relatively less explored modification of proteins.

Thus, there is a need for new molecular targeting agents that could treat a variety of cancers and autoimmune diseases.

DISCLOSURE OF INVENTION

According to the present disclosure, in a first aspect, is a peptoid according to Compound (2):

(2)

In one example of the first aspect is a method of inhibiting a protein comprising an O-GlcN acylted modification comprising contacting the protein with Compound 2.

In another example of the first aspect, the O-GlcN acylation occurs at a threonine or a serine residue.

In another example of the first aspect, the O-GlcN acylation occurs at a serine residue.

In yet another example, the serine residue is S350.

In yet another example of the first aspect, the O-GlcN acylation occurs at a threonine residue.

In another example, the O-GlcN acylated protein is in a T cell or a B cell.

In an example of the first aspect, the method of inhibiting a nuclear factor kappaB (NF-kappaB) protein comprising contacting the NF-kappa B protein with the peptoid according to the first aspect.

In another aspect of the first aspect, the method of inhibiting a nuclear factor kappaB (NF-kappaB) protein where the NF-kappaB protein comprises an O-GlcN acylated modification.

In yet another example of the first aspect, the method of inhibiting a nuclear factor kappaB (NF-kappaB) protein where the O-GlcN acylated modification occurs at a threonine or a serine residue.

In another aspect of the first aspect, the O-GlcN acylated modification occurs at a serine residue.

In another aspect of the first aspect, the method of inhibiting a nuclear factor kappaB (NF-kappaB) protein where the serine residue is S350.

In another aspect of the first aspect, the method of inhibiting a nuclear factor kappaB (NF-kappaB) protein where the O-GlcN acylated modification occurs at a threonine residue.

In yet another aspect of the first aspect, the method of treating or preventing an autoimmune disease comprising administering the peptoid according to the first aspect.

In another aspect of the first aspect, the method of treating or preventing an autoimmune disease comprising administering the peptoid according to the first aspect where the autoimmune disease is diabetes.

In another aspect of the first aspect, the method of treating or preventing diabetes comprising administering the peptoid according to the first aspect where the diabetes is Type I diabetes.

In another aspect of the first aspect, the method of treating or preventing a hyperglycemia-associated disease or condition comprising administering the peptoid according to the first aspect.

In another aspect of the first aspect, the method of treating or preventing a hyperglycemia-associated disease or condition comprising administering the peptoid according to the first aspect where the hyperglycemia-associated disease or condition is selected from the group consisting of Type I diabetes, Type II diabetes, and obesity.

In yet another aspect of the first aspect, the method of treating a cancer comprising administering the peptoid according to the first aspect.

In another aspect of the first aspect, the method of treating a cancer comprising administering the peptoid according to the first aspect where the cancer is a cancer presenting increased O-GlcNAcylation.

In another aspect of the first aspect, the method of treating a cancer comprising administering the peptoid according to the first aspect where the cancer is a blood cancer.

In another aspect of the first aspect, the method of treating a cancer comprising administering the peptoid according to the first aspect where the cancer is selected from the group consisting of acute lymphocytic leukemia, acute myeloid leukemia, chronic lymphocytic leukemia, chronic myeloid leukemia, hairy cell leukemia, diffuse large B-cell lymphoma, mantle cell lymphoma, follicular lymphoma, marginal zone lymphoma, Acute lymphoblastic leukemia, non-Hodgkin's lymphoma, Hodgkin's lymphoma, and multiple myeloma.

In yet another aspect of the first aspect, the method of treating a cancer comprising administering the peptoid according to the first aspect where the peptoid according to the first aspect is co-administered with one or more chemotherapeutic agents.

In another aspect of the first aspect, the method of treating a cancer comprising administering the peptoid according to the first aspect where the peptoid according to the first aspect is administered as monotherapy.

In yet another aspect of the first aspect, the method of treating a cancer comprising administering the peptoid according to the first aspect where the cancer is a metastatic cancer.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary and are intended to provide an overview or framework to understanding the nature and character of the claims. The accompanying drawings are included to provide a further understanding and are incorporated in and constitute a part of this specification. The drawings illustrate one or more embodiments, and together with the description, explain principles and operation of the various embodiments. Directional terms as used herein—for example, up, down, right, left, front, back, top, bottom—are made only with reference to the figures as drawn and are not intended to imply absolute orientation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features, examples and advantages of aspects or examples of the present disclosure are better understood when the following detailed description is read with reference to the accompanying drawings, in which.

DETAILED DESCRIPTION

Example embodiments will now be described more fully hereinafter with reference to the accompanying figures in which example embodiments and representative data are shown. Whenever possible, the same reference numerals are used throughout the drawings to refer to the same or like parts. However, the embodiments may take on many different forms and should not be construed as limited to those specifically set forth herein. These example embodiments are provided so that this disclosure will be both thorough and complete, and will fully convey the scope of the claims to those skilled in the art.

Directional terms as used herein (e.g., up, down, right left, front, back, top, bottom) are made only with reference to the figures as drawn and are not intended to imply absolute orientation.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an endpoint of a range, the disclosure should be understood to include the specific value or endpoint referred to. Whether or not a numerical value or endpoint of a range in the specification recites "about," the numerical value or endpoint of a range is intended to include two embodiments: one modified by "about," and one not modified by "about." It will be further understood that the endpoints of each of the ranges are significant both in relation to the other endpoint, and independently of the other endpoint. That is, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. Herein, when a range such as 5-25 (or 5 to 25) is given, this means preferably at least or more than 5 and, separately and independently, preferably not more or less than 25. In an example, such a range defines independently 5 or more, and separately and independently, 25 or less.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Thus, cells that are "free of" or "substantially free of T cell contamination" for example, are cells to which T cells are not actively added or batched into cell culture, but may be present in very small as a contaminant resulting from natural cell progression during expansion. Similarly, other components may be characterized as "free of" or "substantially free of" in the same manner.

Further, as used herein, the term "consisting essentially of" allows for elements not explicitly recited but excludes element that affect basic or novel characteristics of the inventions. As recited herein, the term "consisting of" excludes elements not expressly stated.

The precise regulation of transcription is essential for productive immune response and prevention of autoimmunity. Type 1 diabetes is an autoimmune disorder in which self-reactive T cells destroy insulin producing pancreatic beta cells. Deficiency of insulin leads to hyperglycemia, which is a defining characteristic of autoimmune diabetes. One of the pathological consequences of hyperglycemia is aberrant posttranslational modification of cellular proteins in a process called O-GlcNAcylation. It is a reversible intracellular posttranslational modification that occurs in the cytoplasm and nucleus. It involves attachment of the sugar N-acetylglucosamine (GlcNAc) to the serine and threonine residues in nuclear cytoplasmic proteins. See, e.g., Hart, G. W., M. P. Housley and C. Slawson (2007). "Cycling of O-linked beta-Nacetylglucosamine on nucleocytoplasmic proteins." Nature 446(7139): 1017-1022. Analogous to phosphorylation, modification by O-GlcNAc is a dynamic process, mediated by the enzymes O-GlcNAc transferase (OGT) for the addition and GlcNAcase (OGA) for the removal of O-GlcNAc from proteins. O-GlcNAcylation levels play an important role in nearly all cellular processes, including cell cycle, transcription, translation, protein stability, protein interactions, cellular stress and immune functions. Lack of O-GlcNAcylation is embryonically lethal.

It is known that hyperglycemia induces O-GlcNAcylation of the transcription factor, nuclear factor kappaB (NF-kappaB) protein subunit, c-Rel at serine 350, in T cells. Ramakrishnan, P. et al. Activation of the Transcriptional Function of the NF-kappaB Protein c-Rel by O-GlcNAc Glycosylation. Science Signaling 6, ra. 75 (2013). NK-kappaB is a pleiotropic, evolutionarily conserved transcription factor family that plays a central role in regulating autoimmunity, inflammation, cell survival, and apoptosis in several disorders, including Type 1 diabetes. O-GlcNAcylation has been shown to be important for the activation of NF-kappaB in T and B-lymphocytes and its role in inflammation and diabetes is emerging. High glucose and glucosamine levels can elevate O-GlNAcylation of several proteins including NF-kappaB and enhance its transcription. Related findings suggest a possible overlap in functions of NF-kappaB c-Rel and O-GlcNAcylation. C-Rel is essential for T cell function and the expression of the transcription factor fork head box P3 (FOXP3) that controls T regulatory (T reg) cell development. T cells play a major role in autoimmune diabetes. CD4$^+$ T cells produce cytokines such as interleukin-2 (IL-2), interferon gamma (IFNG) and granulocyte-macrophage colony-stimulating factor (GMCSF), which promotes autoimmunity by stimulating the cytotoxic activity of CD8$^+$ T cells as well as by activating innate immune cells.

It is further known that O-GlcNAcylation of c-Rel enhances the expression of c-Rel-dependent Th1 cytokinases IL-2, IFNG, and GMCSF, in activated T cells (Ramakrishnan, 2013). It has now been determined that O-GlcNAcylation of the NF-kappaB subunit c-Rel modulated its transcriptional activity in T lymphocytes in a way that may aggravate autoimmunity. Thus, once diabetes originates, the patient develops hyperglycemia. This increases O-GlcNAcylation of c-Rel, which may play a role in exacerbating T cell-mediated autoimmunity by positively regulating proautoimmune cytokine expression.

Increased O-GlcNAcylation is also now been implicated in many cancers, especially in transcriptional regulation, survival, cell proliferation and metastasis. Clinical behavior of Chronic Lymphocytic Leukemia (CLL) cells has been reported to correlate with intensity of O-GlcNAcylated protein levels in those cells. Expression of hexosamine biosynthetic pathway (HBP) enzymes as well as global GlcNAcylation is increased in Acute myeloid leukemia (AML) patients and its inhibition is known to result in AML cell apoptosis, sparing normal cells. On the other hand, moderate HBP or O-GlcNAcylation inhibition induces AML cell differentiation, suggesting that AML cells increasingly depend on HBP and O-GlcNAcylation for their survival and maintaining an undifferentiated state. Surprisingly, NF-kappaB c-Rel has been revealed as a major O-GlcNAcylated protein in AML cells, and aberrant c-Rel function has been reported in various myeloid and lymphoid malignancies.

In order to provide new treatment strategies that could work against autoimmune diseases, cancers and other disease states that implicate high levels of O-GlcNAcylated proteins, herein is reported a peptoid that has been designed, synthesized and found to specifically bind to O-GlcNAcylated c-Rel. As used herein, "peptoid" or "peptoids" refers to a peptidomimetic molecule that is derived from the same basic backbone scaffold as a peptide, but as its side chains projecting from the nitrogen rather than from the alpha carbon. Peptoids have superior therapeutic value due to their proteolytic stability and cell permeability. With the ability to form helices, loops and turns, peptoids are able to access an array of structural diversity to rival the substrate recognition of their natural peptide counterparts. Among other things, peptoids have been developed as potent inhibitors of protein/protein interactions associated with disease states. Peptoids have the advantage of much greater chemical diversity than peptides while maintaining many of the structural features of peptides, which make them an ideal platform suited for simple translation of peptides to potential therapeutics.

According to the present disclosure is a peptoid that was designed de novo, synthesized and tested for its ability to block the function of O-GlcNAcylated c-Rel specifically without toxicity. In one aspect is a peptoid according to Compound 1, (1)

wherein $R^1$, $R^2$, $R^3$, $R^4$, and $R^5$ are independently selected from hydrogen, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3{}^a$, —N(R$^a$R$^b$), —C(O)N(R$^a$R$^b$), —SO$_2$N(R$^a$R$^b$), —SO$_2$N(R$^a$R$^b$), —NR$^c$C(O)R$^a$, and the like, wherein $R^a$ and $R^b$ are likewise independently selected from optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl.

Suitable optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds.

In one embodiment of the present disclosure is a peptoid according to Compound 2

(2)

Compound 2 is also known as OGC350. Also contemplated herein are scrambled versions of Compound 2. As used herein, a "scrambled peptoid" is a peptoid that comprises the same tetrameric structure of Compounds 1 and 2, wherein the sidechains are identical but protrude from the amine backbone in a different order from, for example, Compound 2.

In another embodiment of the present disclosure is the peptoid according to Compound 3, a scrambled version of Compound 2.

(3)

As described in the Examples below, the peptoids of the present disclosure have been found to block the function of O-GlcNAcylated c-Rel specifically and with no substantial toxicity. Thus, the compounds of the present disclosure can be used as specific inhibitors for the treatment of disease states associated with elevated levels of O-GlcNAcylated proteins, and in particular, O-GlcNAcylated c-Rel.

Conditions for prevention or treatment with the peptoids of the present disclosure include any disease or condition wherein levels of O-GlcNAcylated protein levels are elevated. In one aspect, a condition for prevention or treatment with the peptoids of the disclosure is an autoimmune disease. The disclosure contemplates use of the peptoids according to Compound 1 for use with a variety of autoimmune diseases or conditions wherein c-Rel function has been implicated. Exemplary conditions or diseases include, for example, multiple sclerosis, celiac disease, rheumatoid arthritis, psoriasis, inflammatory bowel disease, diabetes, and lupus. In an exemplary embodiment, the autoimmune disease is diabetes, and in particular, Type 1 diabetes. In another aspect, the disease or condition is a hyperglycemia-associated disease or condition. In an exemplary embodiment, the hyperglycemia-associated disease or condition is Type I diabetes, Type II diabetes, or obesity. In yet another aspect, a condition for prevention or treatment with the peptoids of the disclosure is a cancer. In an exemplary embodiment, the cancer is a blood cancer, including but not limited to acute lymphocytic leukemia, acute myeloid leukemia, chronic lymphocytic leukemia, chronic myeloid leukemia, hairy cell leukemia, diffuse large B-cell lymphoma, mantle cell lymphoma, follicular lymphoma, marginal zone lymphoma, Acute lymphoblastic leukemia, non-Hodgkin's lymphoma, Hodgkin's lymphoma, or multiple myeloma. In another exemplary embodiment, the cancer is a metastatic cancer.

The peptoids disclosed herein may be administered to a patient in need thereof. In one aspect, the peptoids according the disclosure may be administered as monotherapy to treat or prevent a disease or condition associated with elevated levels of O-GlcNAcylated proteins. In other aspect, the peptoids may be administered in combination with one or more other therapies or therapeutic agents. In one aspect, the peptoid may be co-administered in combination with more or more additional chemotherapeutic agents.

The peptoids of the present disclosure can be administered to a patient in need thereof in the form of a pharmaceutical composition. Such a pharmaceutical composition could be, for example, a composition suitable for oral, parenteral, or sublingual administration. The composition may be formulated with one or more pharmaceutically acceptable excipients depending on the route of administration.

The following examples are illustrative and are not intended to limit the scope of the invention as claimed.

EXAMPLES

Example 1—De Novo Peptoid Design

Figure 1:
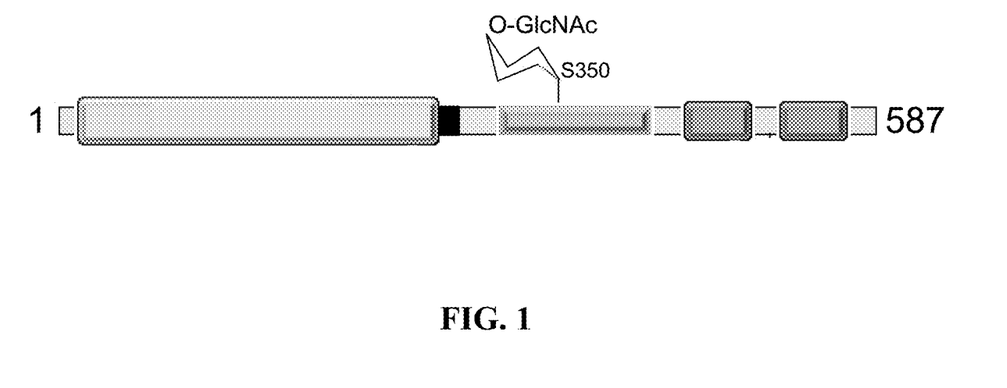
FIG. 1 is a schematic representation showing O-GlcNAcylation of c-Rel at S350.
Figure 2:
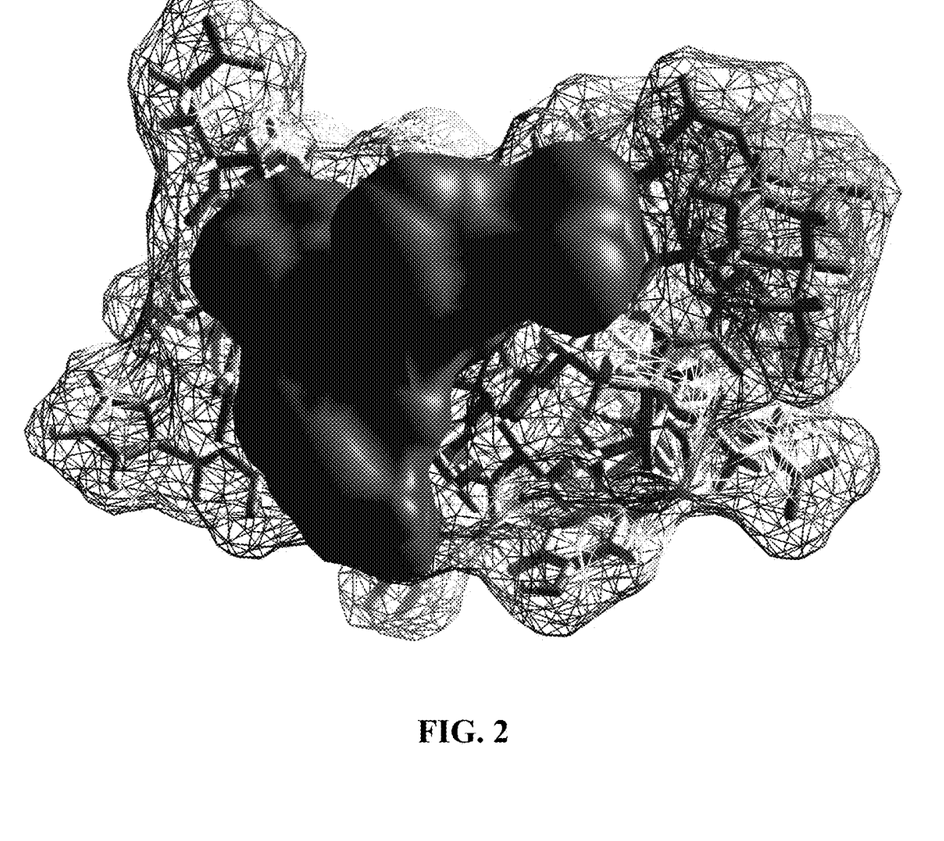
FIG. 2 shows a molecule modeling representation of Compound 2 bound to the O-GlcNAcylation c-Rel peptide.

It is known that c-Rel is O-GlcNAcylated at a single serine residue 350 and that this modification activates the CD28-responsive element-dependent transactivation potential of c-Rel. Thus, fragment of the solvent-exposed c-Rel domain of 30 amino acids surrounding S350 was studied. The 30 amino acid sequence of 331 to 360 was input into the protein folding simulator package PepFold (Thevenet et al, 2012). Using the program, a consensus protein fold was determined, from which a modified, coarse-grained, energy-minimized model of the S350 O-GlcNAcylated c-Rel peptide was found using the manual docking of GlcNAc to S350 using the Chem3D software package (CambridgeSoft, Perkin Elmer Informatics). Molecular modeling indicated that S350 is solvent exposed and protrudes from hydrophobic pockets. Based on this model, peptoids were iteratively designed in silico for interaction at the solvent exposed GlcNAc-c-Rel interface and docked using Autodock Vina. The peptoid with the highest affinity (i.e. lowest energy score) was a tetramer, Compound 2, which is shown in red in FIG. 2 bound to in the O-GlcNAcylated c-Rel peptide. These modeling studies show that Compound 2 interacted specifically with the O-GlcNAcylated c-Rel peptide and was selected for its projected low millimolar binging affinity.

Example 2-Solid Phase Peptoid Synthesis

Compound 2 and a scrambled peptoid as a negative control, Compound 3 which was derived from the same residues but arranged in a different order, were synthesized using standard submonomer synthetic procedures. More specifically, Rink resin (Chem-Impex) was swelled in DMF for 1 hour. The resin was drained under vacuum and washed with DMF and DCM. The terminal FMOC group was deprotected using 20% 4-methylpiperidine in DMF (20 min). The resin was washed with DMF followed by DCM and deprotection was confirmed via a Kaiser test. A solution of chloroacetic acid (2.0 M) and DIC (2.0 M) in DMF was added to the resin. The resulting slurry was shaken at 37° C. for 10 minutes. The resin was drained and washed with DMF followed by DCM. Subsequently a 2.0 M solution of primary amine in NMP was added to the resin and allowed to shake for 2 h at 37° C. The resin was drained and washed with DMF and DCM. The presence of secondary amines was confirmed through chloranil testing. The submonomer process was repeated until the full-length peptoid was synthesized on resin. Upon completion of the peptoid oligomer, the resin was washed with DCM and then immersed in a 95% TFA, 2.5% TIPS and 2.5% water solution for 2 h. The solvent was collected by vacuum filtration and evaporated under a stream of air. The resulting crude product was partitioned between microcentrifuge tubes and precipitated from cold diethyl ether. The tubes were briefly centrifuged as maximum speed in a microcentrifuge and the solvent was decanted. This process was repeated three times to isolate crude peptoids as brown oils. The crude products were dissolved in water and purified by reverse phase HPLC (C:18 (Agilent)). Peptoid identity was confirmed by mass spectroscopy (Compound 2: Predicted m/z: 501.89 ($M^{30}H^+$), Observed m/z: 502.27 ($M^{30}H^+$); Compound 3: Predicted m/z: 501.89 ($M^{30}H^+$); Observed m/z: 502.31 ($M^{30}H^+$)).

Figure 3:
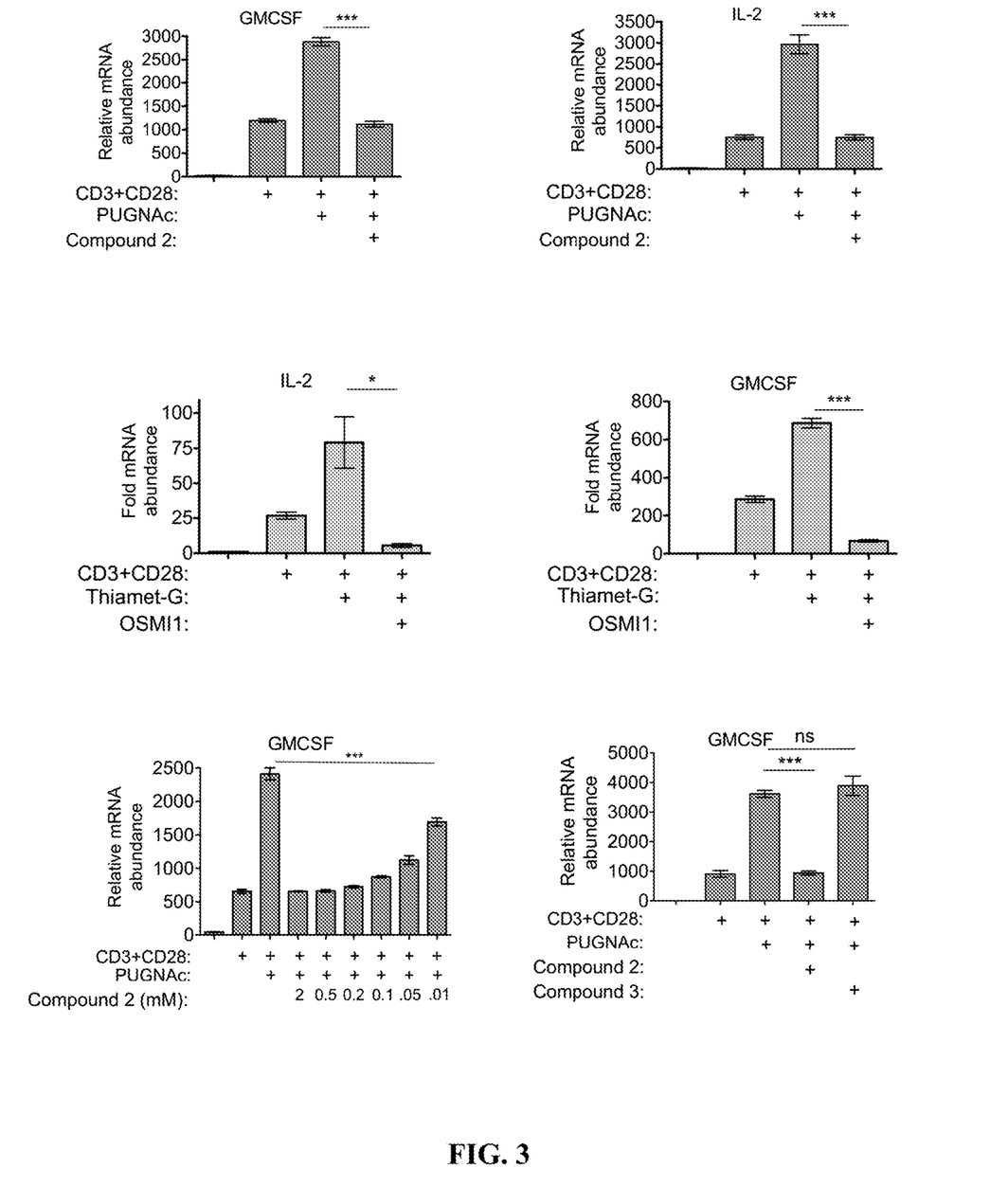
FIG. 3 shows the specific inhibition of O-GlcNAcylation c-Rel upon treatment of Jurkat T cells with Compound 2.

Example 3-Compound 2 Specifically Inhibits O-GlcNAcylation-Dependent c-Rel Activity C-Rel has been shown to be essential for the induction of genes such as GMCSF and IL-2 following co-stimulation of CD3 and CD28 receptors in T cells (Ramakrishnan, 2013). It is further known that a mutation of c-Rel at S350 completely abrogates T cell receptor (TCR)-induced O-GlcNAcylation-dependent expression of GMCSF and IL-2 (Ramakrishnan, 2013). Thus, the specific inhibition of c-Rel O-GlcNAcylation by Compound 2 was studied. Jurkat cells were grown in RPMI medium at $1 \times 10^6$ cells/2 mL. The cells were treated with compound 2 (100 μM and 200 μM) for 16 hours. Cell death was assessed by propidium iodide (Biolegend) staining and flow cytometry. Following treatment with Compound 2, the resulting expression of GMCSF and IL-2 was measured. FIG. 3 confirms that expression of GMCSF (top left) and IL-2 (top right) was significantly decreased upon exposure to Compound 2 (right bars). Further, treatment with Compound 2 specifically affected only the O-GlcNAcylation-dependent enhancement of IL-2 and GMCSF expression. It did not block the TCR-induced expression levels of these genes. In contrast, treatment with the global O-GlcNAcylation inhibitor OSMI1 (Sigma Aldrich) suppressed the expression of GMCSF and IL-2 well below the TCR-induced levels (FIG. 3, middle panels). This indicates specificity of Compound 2 towards O-GlcNAcylated c-Rel, suggesting that the normal IL-2 and GMCSF expression by T cells, and T cell homeostasis, should be maintained following treatment with Compound 2.

The range of concentrations at which Compound 2 is effective in suppression O-GlcNAcylation c-Rel function was studied. Jurket cells were exposed to Compound 2 in concentrations of 2 mM, 500 μM, 200 μM, 100 μM, 50 μM and 10 μM peptoid on TCR-induced GMCSF expression. As shown in FIG. 3, bottom left, treatment with 200 μM Compound 2 can cause near complete suppression of O-GlcNAcylation-dependent GMCSF expression. Exposure at higher concentrations of 500 μM and 2 mM did not further decrease GMCSF expression levels. Notably, at these higher concentrations no non-specific decrease in GMCSF expression was observed, suggesting cells can tolerate high concentrations of Compound 2.

The effect of the scrambled peptoid, Compound 3, was also studied (FIG. 3, bottom right panel). While Compound 3 suppressed GMCSF expression, no inhibitory effect was observed, demonstrating the specificity of Compound 2.

Figure 4:
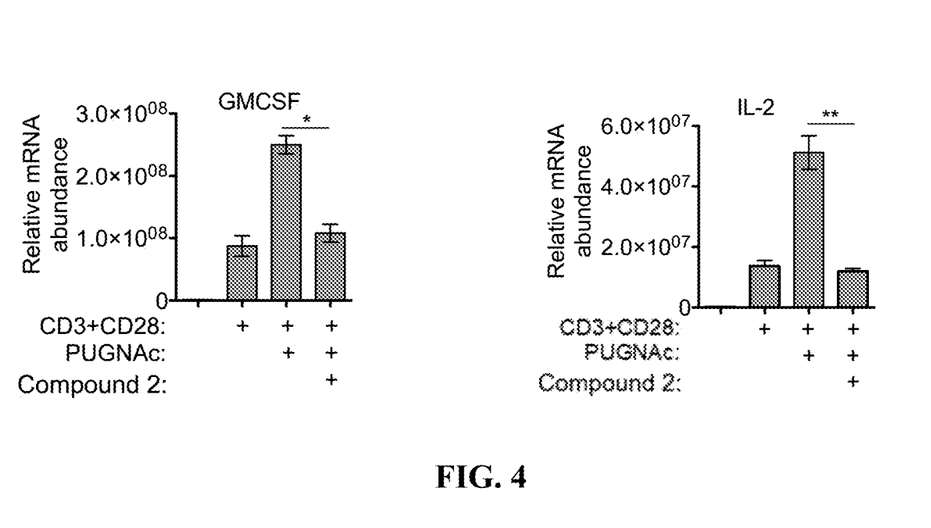
FIG. 4 shows the specific inhibition of O-GlcNAcylation c-Rel upon treatment of human primary T cells with Compound 2.

Example 4-Compound 2 Blocks TCR-Induced O-GlcNAcylated-c-Rel-Dependent Function in Primary T Cells The effect of Compound 2 was studied in primary CD4+ T cells isolated from human peripheral blood mononuclear cells. CD4+ T cells were collected from the spleen of normoglycemic non obese diabetic (NOD) mice were isolated by magnetic sorting (Miltenyi Biotec) and cultured in supplemented RPMI medium. Cells were treated with 100 μM of Compound 2 twice—at the start of the experiment and at 24 hrs. Anti-CD3 and anti CD28 antibodies (Biolegend) were studied and TCR activation and cell proliferation were performed as described (Ramakrishnan et al. "Deficiency of Nuclear Factor-kappaB c-Rel Accerlates the Development of Autoimmune Diabetes in NOD Mice." Diabetes 65, 2367-2379 (2016). As shown in FIG. 4, Compound 2 (100 µM) effectively and significantly decreased TCR-induced O-GlcNAcylation-dependent increases in the expression of GMCSF and IL-2 in human primary T-cells. Treatments with Compound 2 specifically affected only the O-GlcNAcylation-dependent enhancement of GMCSF and IL-2 expression. Compound 2 did not block the TCR-induced expression level of these genes or other NF-kappaB-induced genes such as A20 and I-kappa-B-alpha. Thus, Compound 2 demonstrates specificity in primary T cells, and suggests that the normal IL-2 and GMCSF expression by T cells will be maintained in primary T cells following treatment with Compound 2.

Compound 2 was further studied in B cells (BJAB) and macrophages (RAW 264.7). BJAB cells were grown in RPMI medium and RAW 264.7 cells were grown in DMEM medium supplemented with 100 U/mL penicillin/streptomycin, 4 mM L-glutamine and 10% fetal bovine serum. It was found that Compound 2 does not exhibit any non-specific activity across cell types.

Example 5—Compound 2 Toxicity Studies

Figure 5:
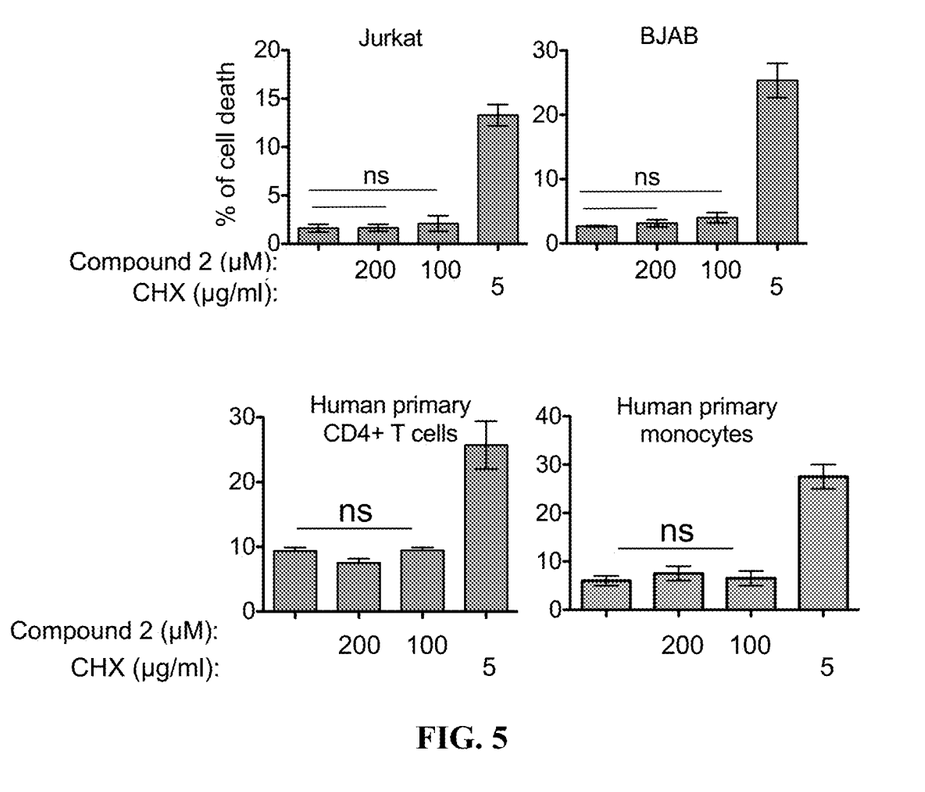
FIG. 5 reports toxicity studies of Compound 2 on Jurkat (left), BJAB B cells (middle) and human primary T cells (right).

The toxicity of Compound 2 was studied at 100 µM and 200 µM concentrations in Jurket cells (FIG. 5, left), BJAB B cells (FIG. 5, middle left), human primary CD4+ T cells (FIG. 5, middle right), and human primary monocytes (FIG. 5, right). Cell death was assessed by propidium iodide staining and flow cytometry. It was found that treatment with up to 200 µM of Compound 2 resulted in non-significant cell death (indicated as "ns") in all cell types tested. In other words, Compound 2 did not show any toxicity at concentrations of 100 µM and 200 µM at 40 hours post-treatment. Treatment with cycloheximide (CHX) (Sigma Aldrich), a generic inhibitor of translation, was used as a positive control for cell death induction. At 16 hours post-CHX treatment (5 µg/mL), all three cell types showed significant cell death in the presence of CHX.

Example 6—Compound 2 Blocks DNA Binding of O-GlcNAcylated c-Rel

Figure 6:
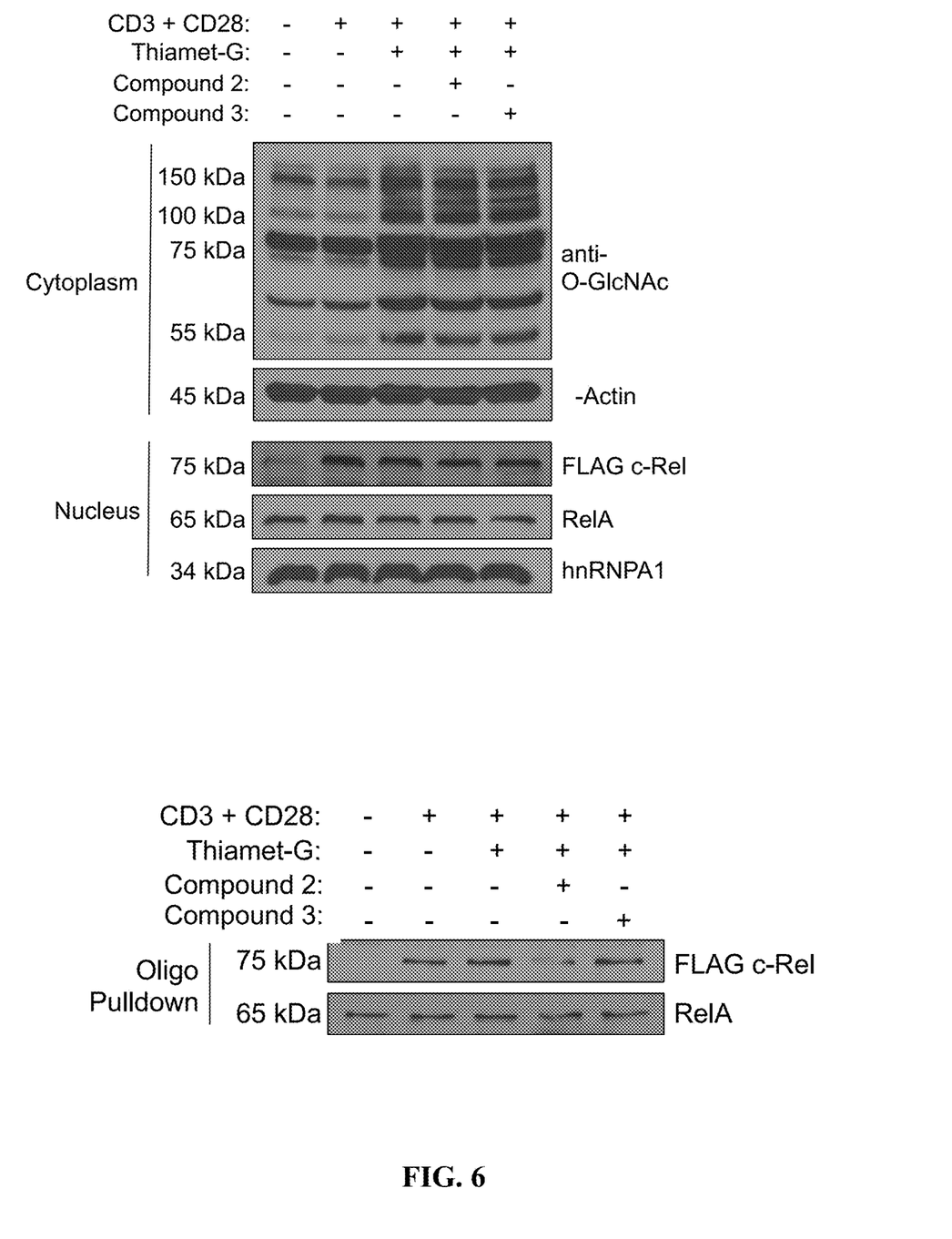
FIG. 6 shows the Compound 2 blocking function on DNA binding.

Activation of c-Rel involves signal-induced translocation of c-Rel from the cytoplasm to the nucleus and its subsequent DNA binding and gene expression. Thus, the effect of treatment with Compound 2 and Compound 3 (comparative) on nuclear translocation of c-Rel were examined. Cytoplasmic and nuclear extracts were prepared and Western blotting was performed as described in DeJesus, T. J. and Ramakrishnan, P. "NF-kappaB c-Rel Dictates the Inflammatory Threshold by Acting as a Transcriptional Repressor." iScience 23, 100876 (2020). As shown in FIG. 6 (top), no significant change in nuclear c-Rel levels was observed for either peptoid. Thus, Compound 2 does not affect nuclear translocation of c-Rel.

Oligonucleotide pull down assays were performed to examine whether Compound 2 binds to O-GlcNAcylated c-Rel and thus, competitively prevents its binding to CD28RE. Jurket cells were treated with anti-CD3/CD28 antibodies to trigger TCR activation and c-Rel nuclear translocation. Cells were contacted with Thiamet-G (an O-GlcNAse inhibitor) (Sigma Aldrich) to enhance cellular O-GlcNAcylation. It was found that TCR activation and enhanced O-GlcNAcylation caused enhanced binding of c-Rel to the CD28RE DNA (data not shown). Addition of Compound 2 (50 µM) reduced the binding of c-Rel, while the scrambled peptoid, Compound 3, did not block the binding of c-Rel (FIG. 6, bottom). This demonstrates that Compound 2 specifically inhibits c-Rel binding to CD28RE by blocking its function and controls the expression of TCR-induced c-Rel dependent genes such as GMCSF and IL-2, which regulate autoimmunity. No such effect was observed for Compound 3.

Example 7—O-GlcNAcylation is Elevated in AML Cells

Figure 7:
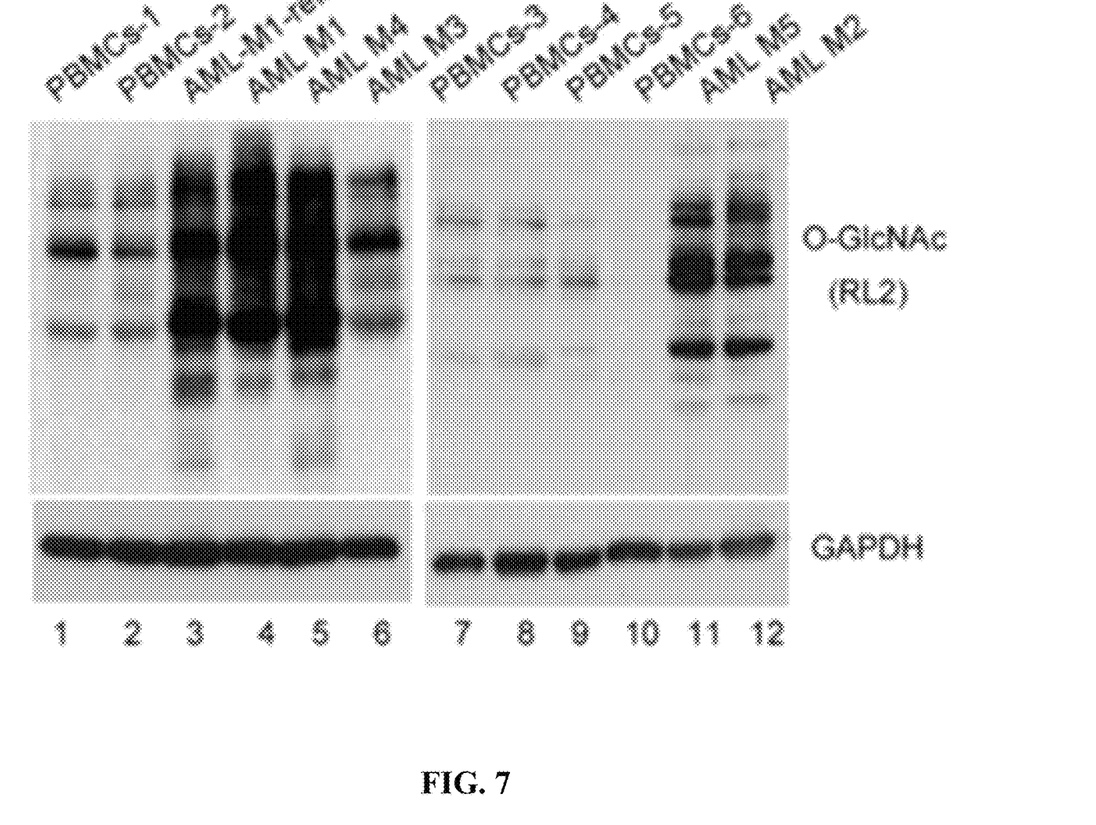
FIG. 7 shows elevated levels of O-GlcNAcylation in AML cells.

Normal cells and primary AML cells isolated from human patients were obtained from the Hematopoietic Stem Cell Core Facility located at Case Western Reserve University. The Western blot shown in FIG. 7 demonstrates that for four different AML subtypes (M1, M2, M4 and M5) as well as a relapsed AML-M1 patient sample exhibit greatly enhanced global O-GlcNAcylation (bands 3, 4, 5, 11 and 12) as compared to normal PBMCs (bands 1, 2, 7, 8, 9 and 10). Thus, O-GlcNAcylated proteins in cancers expressing high levels of O-GlcNAcylated proteins, e.g. AML, are targets for treatment with Compound 2.

To identify specific O-GlcNAcylated proteins in AML, total O-GlcNAcylated proteins in the leukemia cell line K562 were isolated using a generic antibody that detects cellular O-GlcNAcylatedproteins. Cells ($100 \times 10^6$) were treated with PUGNAc (Sigma Aldrich) overnight, lysed and immunoprecipitated with IgG or RL2 antibodies and stained with Coomassie blue. The c-Rel band of NF-kappaB (MW 75 kDa) was confirmed by mass spectroscopy. Confirmation of O-GlcNAcylated c-Rel peptide was done using a monoclonal antibody that detected S350 O-GlcNAcylated c-Rel peptide (data not shown).

Figure 8:
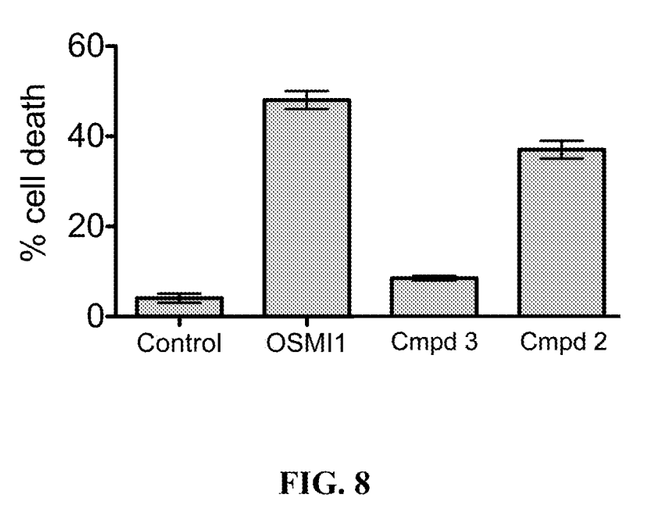
FIG. 8 shows cell death following treatment with Compound 2 in a leukemia cell line.

Example 8—Compound 2 Blocks O-GlcNAcylated c-Rel Function in AML Cells and Induces AML Cell Death The effect of Compound 2 on AML cells was studied. Leukemia K562 cells were treated with HBP inhibitor OSMI1 (50 µM) or Compound 2 (100 µM). Scrambled peptoid Compound 3 was used as a control. FIG. 8 shows that the K562 cell death (y-axis) resulting from treatment with Compound 2 (right bar) is nearly comparable to that caused by known OGT inhibitor OSMI1 (left middle bar). Scrambled peptoid Compound 3 resulted in no significant cell death (right middle bar), confirming that specific blocking of O-GlcNAcylated c-Rel by Compound 2 is leading to AML cell death.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:

1. A peptoid of Compound 2:

(2)

2. A method of inhibiting a protein comprising an O-GlN acylated modification comprising contacting the protein with the peptoid of claim 1, wherein protein is an O-GlcN acylated c-Rel nuclear factor kappa B (NF-kappaB) protein.

3. The method according to claim 2, wherein the O-GlcN acylation occurs at S350 residue.

4. The method according claim 2, wherein the O-GlcN acylated protein is in a T cell or a B cell.

5. A method of treating a cancer comprising administering the peptoid of claim 1 wherein cancer is acute myeloid leukemia.

6. The method according to claim 5 wherein the cancer is a cancer presenting increased O-GlcNAcylation.

7. The method according to claim 5, wherein the peptoid is co-administered with one or more chemotherapeutic agents.

8. The method according to claim 5, wherein the peptoid is administered as monotherapy.

9. The method according to claim 5, wherein the cancer is a metastatic cancer.

* * * * *